United States Patent [19]

Zeelen et al.

[11] 4,177,197
[45] Dec. 4, 1979

[54] CYCLIZATION SUBSTRATES AND 7α-SUBSTITUTED 19-NORSTEROID DERIVATIVES

[75] Inventors: Filippus J. Zeelen, Heesch; Marinus B. Groen, Schayk, both of Netherlands

[73] Assignee: Akzona Inc., Asheville, N.C.

[21] Appl. No.: 880,151

[22] Filed: Feb. 22, 1978

[30] Foreign Application Priority Data

Feb. 24, 1977 [NL] Netherlands .......................... 7701972

[51] Int. Cl.² .............................................. C07J 3/00
[52] U.S. Cl. ..................... 260/397.5; 260/239.55 R; 260/340.9 AS; 260/340.9 R; 260/345.3; 260/347.91; 260/397.4; 260/448.2 B; 260/586 C; 260/586 E; 260/600 R; 560/55; 568/648
[58] Field of Search ..... 260/397.5; Steroids MS File

[56] References Cited

U.S. PATENT DOCUMENTS

3,660,435  5/1972  Anner et al. ...................... 260/397.5

FOREIGN PATENT DOCUMENTS

1448873  9/1976  United Kingdom ................ 260/239.55

*Primary Examiner*—Ethel G. Love
*Attorney, Agent, or Firm*—Robert H. Falk; Charles A. Wendel; Francis W. Young

[57] ABSTRACT

Novel cyclization substrates are disclosed of the formula

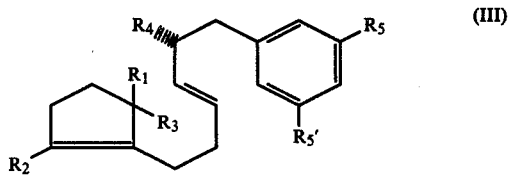

wherein:
(a) $R_1$ is H or alkyl of one to four carbon atoms;
(b) $R_2$ is H or alkyl of one to four carbon atoms, with the proviso that $R_1$ is H when $R_2$ is alkyl, and with the proviso that $R_2$ is H when $R_1$ is alkyl;
(c) $R_3$ is a leaving group selected from the group consisting of hydroxy, alkoxy of one to four carbons, alkoxyalkoxy of two to four carbons, acyloxy of one to about seven carbons, and trialkylsilyloxy of less than fifteen carbons;
(d) $R_4$ is hydrocarbyl of one to four carbon atoms, a hydrocarbyl of one to two carbon atoms substituted by halogen or alkoxy of one to two carbons, or alkoxy of one to four carbon atoms; and
(e) $R_5$ and $R_5'$ each are H, OH, alkyl, trialkylsilyloxy, or an esterified or etherified hydroxy-group of about one to ten carbon atoms.

A method is disclosed for the cyclization of the compounds of formula III leading to novel and biologically active compounds of the following formulae:

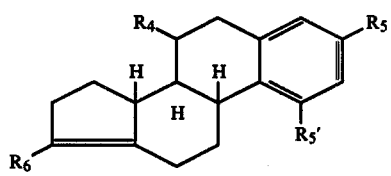

(IV)
"para"

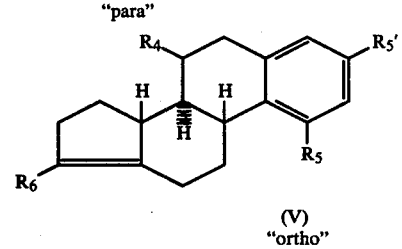

(V)
"ortho"

having $R_1$ through $R_5'$ as defined above, with $R_6$ being alkyl of from one to about four carbon atoms, among which are intermediates for preparing well-known biologically active 7α-substituted steroids, such as 7α-methyl-oestrone; 7α-methoxy-oestradiol and the like.

4 Claims, No Drawings

CYCLIZATION SUBSTRATES AND 7α-SUBSTITUTED 19-NORSTEROID DERIVATIVES

BACKGROUND OF THE INVENTION

1. Field of the Invention

The invention relates to the preparation of novel cyclisation substrates for steroidal compounds, and also relates to the conversion of these cyclisation substrates into novel steroidal compounds, in particular, 7α-substituted steroids of the oestrane series.

2. Prior Art and Other Information

The stereospecific cyclisation of a compound of formula I:

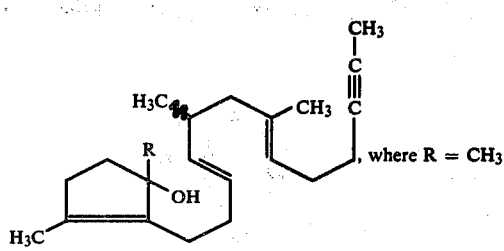

into a compound of formula II:

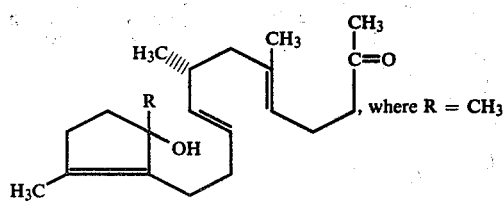

is described in 98 J.A.C.S. 1038 (1976).

Only the equatorial 11α-methyl derivative is formed. The cyclisation of a (pro)-11-hydroxy compound also results exclusively in the 11α-hydroxy steroid (98 J.A.C.S. 1039 (1976)).

When this cyclisation is performed in the (pro)-19-nor-series (R is H), it proves that no stereo-selectivity occurs (see T. M. Yarnell, Dissertation, Stanford University, July 1975, in 1976 DISSERTATION ABSTRACTS INTERN, 1976, B36 no. 10, page 5054). A mixture of 11α- and 11β-substituted steroids in molar proportions of about 1:1 is formed.

Related compounds by structure to those of formulae III-V of the instant invention and processes for converting 1-aryl-8,11-bis(ethylenedioxy)-3-dodecene compounds to 3-alkyl-2-[(E)-6'-(aryl)-3'-hexenyl]-2-cyclopentenones and subsequently via cyclopentenols to 17-substituted-$\Delta^{1,3,5(10),13(17)}$-gonatetraenes are disclosed in British Pat. No. 1 448 873 and 95 J.A.C.S. 7501-7504 (1973).

The present invention provides a method of producing 7α-substituted analogues of the steroidal compounds disclosed in British Pat. No. 1 448 873 (such as 7α-methyl-oestrone by cyclizing 2-[(E)-6-aryl-3-hexenyl]-cyclopentenols of which the hexenyl group has been substituted in position 5. Steroids which may be prepared according to the method of the present invention are disclosed inter alia in U.S. Pat. No. 3,627,894 (7α-methyl-estrones), U.S. Pat. No. 3,574,197 (1-hydroxy-7α-methyl-estrane derivatives), U.S. Pat. No. 3,944,576 (7α-methoxymethyl-estrane derivatives) and U.S. Pat. Nos. 3,318,925/26/27/28/29 (7α-methyl-$\Delta^{1,3,5(10)}$-estratriene derivatives).

SUMMARY OF THE INVENTION

Novel cyclisation substrates are disclosed of the formula:

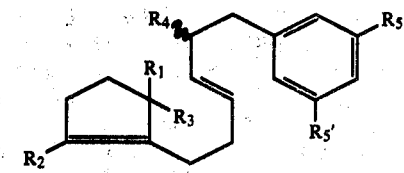

(a) $R_1$ is H or alkyl of one to four carbons;
(b) $R_2$ is H or alkyl of one to four carbons, with the proviso that $R_1$ is H when $R_2$ is alkyl, and with the proviso that $R_2$ is H when $R_1$ is alkyl;
(c) $R_3$ is a leaving group selected from the group consisting of hydroxy, alkoxy of one to four carbons, alkoxyalkoxy of two to four carbons, acyloxy of one to about seven carbons, and trialkylsilyloxy of less than fifteen carbons;
(d) $R_4$ is hydrocarbyl of one to four carbons, a hydrocarbyl of one to two carbon atoms substituted by halogen or alkoxy of one to two carbons, or alkoxy of one to four carbons; and
(e) $R_5$ and $R_5'$ each are H, OH, alkyl, or an esterified or etherified hydroxy-group of one to about ten carbons.

Surprisingly, it has now been found that the cyclisation of a cyclisation substrate with the formula III:

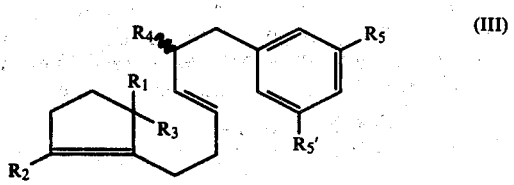

leads stero-specifically to axially-substituted steroidal compounds of formulae IV and V having $R_4$, $R_5$ and $R_5'$ as described above:

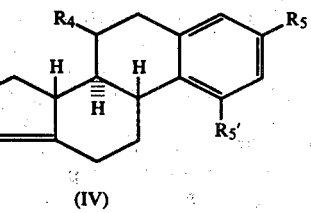

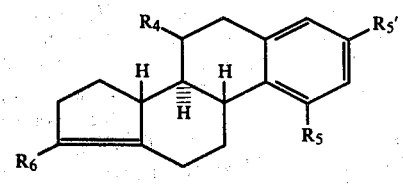

which after rotation, may be represented in shorthand notation by the formula:

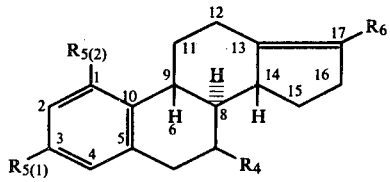

(IV-V)

where $R_{5(1)}$ is $R_5$ when $R_{5(2)}$ is $R_5'$ and $R_{5(1)}$ is $R_5'$ when $R_{5(2)}$ is $R_5$, and which is more recognizable to those skilled in the art. $R_6$ is an alkyl moiety of from one to about four carbon atoms.

In formulae III, IV and V, most preferably $R_1$ and $R_2$ are H or $CH_3$, $R_3$ is OH, $R_4$ is $CH_3$, $R_5$ is $OCH_3$ or trialkylsilyloxy of three to twelve carbons, $R_5'=H$ and $R_6$ is $CH_3$.

When $R_5$ is $R_5'$, the resultant compounds are identical; when $R_5$ is not $R_5'$, the cyclisation results in two isomers, the proportions of which are strongly influenced by the cyclisation conditions and the choice of the substituents $R_5$ and $R_5'$.

DESCRIPTION OF THE PREFERRED EMBODIMENTS

The cyclisation substrates of formula III are novel compounds which may be prepared in several ways each of which are known to those skilled in the relevant pharmaceutical arts. The invention is therefor also characterized by the preparation of novel compounds with the general formula III in ways which are in themselves known to those in the relevant art. The invention is also characterized by the cyclisation of the novel cyclisation substrates of formula III to the novel and biologically active axially-substituted steroid compounds of formulae IV and V.

Referring to the Flow Diagram below, the cyclisation substrate III may, for example, be prepared through a series of steps, first by condensing in Reaction (or step) (a) an $\alpha$-$R_4$-$\beta$-arylpropanal (VI) with an $\omega$-$R_2$-5,5,8,8-tetra-alkoxyoctylidene-tri-arylphosphorane (VII or Wittig reagent), or the tetraalkyl thio-analogue thereof, under conditions which favor the E-configuration (Wittig-Schlosser reaction, see, for example, German Patent Specifications Nos. 1,270,545 and 1,279,678, and 5 ANGEW. CHEMIE, Int. Ed. 126 (1966).

The (E)-olefine-diketal (VIII) obtained is hydrolysed in step (b) under weakly acid conditions to a 1-aryl-8,11-di-oxo-11-alkyl-3-undecene (IX), after which the di-oxo compound (IX) is condensed to a 2-(6'-aryl-3'-hexenyl)-3-alkyl-2-cyclopenten-1-one (X). (Step (c)).

When $R_2$ is alkyl of one to four carbon atoms, the ketone obtained is reduced to an alcohol; and when $R_2$ is H, the ketone is reacted with a compound $R_1Li$ or $R_1Mg$ halogen.

($R_1$ is alkyl (1–4 C)) to give a tertiary alcohol. The OH-group is optionally further esterified or etherified as known to those in the art.

It should be noted that the compound of formula VIII, where $R_4$ is alkoxy, can also be prepared by allowing $\omega$-$R_2$-6,9-bis(alkylidene-dichalcogen)-1-nonynyl-lithium (XIV) to react with an aryl-acetaldehyde (XV), and reducing the 1-(aryl)-2-hydroxy-8,11-bis(alkylidene-dichalocogen)-11-$R_2$-3-undecyne (XVI) thus obtained to the corresponding undecene, followed by etherification of the 2-hydroxy group, according to the scheme:

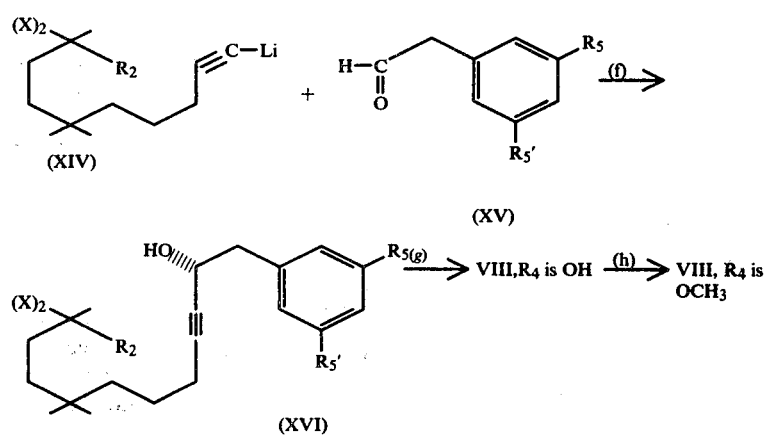

The cyclisation substrate (III) obtained in Reaction (d) is subsequently cyclised with a Lewis acid under acid conditions, to give a tetracyclic compound with an axial $R_4$-substituent.

In the cyclisation Reaction (step e), an effective amount of an aprotic or a protic Lewis acid is used and the reaction is performed in a non-nucleophilic protic or aprotic solvent. Examples of suitable solvents are formic acid, acetic acid, trifluoro-acetic acid, trifluoro-ethanol, benzene, saturated hydrocarbons such as pentane, hexane, cyclohexane, and halogenated hydrocarbons such as dichloromethane.

Examples of protic Lewis acids are carboxylic acids with a pK (20° C.) of less than about 4, and preferably less than about 2, such as, for example, trifluoro-acetic acid, trichloro-acetic acid, formic acid.

Examples of aprotic Lewis acids are stannic chloride, titanium tetrachloride, zinc chloride, zinc bromide, boron trifluoride. Aprotic Lewis acids are preferably used, in an amount of about 0.1 to about 10 moles per mole cyclisation substrate, and preferably about 0.5 to about 5 moles per mole. Stannic chloride is preferable.

The cyclisation reaction is usually carried out at a temperature below room temperature (about 20°–22° C.) and above −150° C. preferably at a temperature between about +10° C. and about −100° C.

The mixtures of "ortho"- and "para"- products ("ortho"=A-aromatic steroid substituted in position 1, "para"=A-aromatic steroid substituted in position 3 of compound IV-V, or compounds (IV/V, but rotated 180°) obtained in the cyclisation step (e) may be separated in the usual way known to those in the art, for example, by chromatography or by crystallization. Racemates of intermediate or final products may be resolved to give the optical antipodes in the usual way.

As to the reaction steps (a)–(e) the following additional information can be given:

Reaction step (a) is usually carried out at a temperature between about $-100°$ C. and about $0°$ C., preferably between about $-75°$ C. and about $-25°$ C. The solvent is usually an etheric solvent, such as diethyl ether, tetrahydrofuran and mixtures thereof. A preferred solvent is an 1:1 mixture of diethyl ether and tetrahydrofuran.

Reaction step (b) is usually carried out at a temperature between about $20°$ C. and $80°$ C., preferably between about $50°$ C. and $60°$ C. The solvent may be an etheric solvent, such as dimethoxyethane, or a mixture of water and an alcohol, such as ethanol. An 1:2 mixture of water and ethanol containing between 5 and 10 mmol HCl per liter, is very suited.

Reaction step (c) is usually carried out between about $60°$ C. and $80°$ C., preferably at about $80°$ C. The solvent is the same as used in step (b). An 1:2 mixture of water and ethanol containing between 5 and 10 mmol NaOH or an equivalent amount of KOH or trimethylbenzylammoniumhydroxide is very suited.

Reaction step (d): The reduction of the ketone to an alcohol is carried out with a complex metallic hydride, such as lithiumaluminiumhydride, di-isobutyl-aluminium-hydride, sodium-di-isobutylboronhydride, at a temperature between about $-50°$ C. and $0°$ C., preferably between about $-25°$ C. and $0°$ C. The reaction of the ketone with a compound $R_1Li$ or $R_1Mg$ halogen is usually carried out at a temperature between $-70°$ C. and $0°$ C., preferably between $-70°$ C. and $-20°$ C. The solvent is usually an etheric solvent, preferably diethyl ether.

The reaction steps (a), (d), (e) and (f) are preferably carried out in an inert atmosphere (nitrogen or argon blanket).

Reaction step (e): When using a protic solvent, preferably a protic Lewis acid is used. A protic solvent, such as formic acid, trifluoro-acetic acid, trifluoroethanol, may also serve as protic Lewis acid. An aprotic solvent may be combined with either a protic Lewis acid or an aprotic Lewis acid.

Reaction step (f) is usually carried out in a solvent, such as diethyl ether, dimethylformamide, dimethylsulfoxide, benzene, toluene, at a temperature between $-70°$ C. and $-25°$ C., preferably between $0°$ C. and $20°$ C.

Reaction step (g): This reduction is preferably carried out with lithiumaluminiumhydride in tetrahydrofuran at a temperature between about $30°$ C. and $60°$ C., preferably between $55°$ C. and $58°$ C.

Reaction step (h) is carried out in an inert solvent, such as xylene or tetrahydrofuran, preferably in tetrahydrofuran in the presence of hexamethylphosphoramide. The "methylating" agent is a methylhalide or dimethylsulphate, preferably methyliodide. The base is preferably a metalhydride such as sodiumhydride.

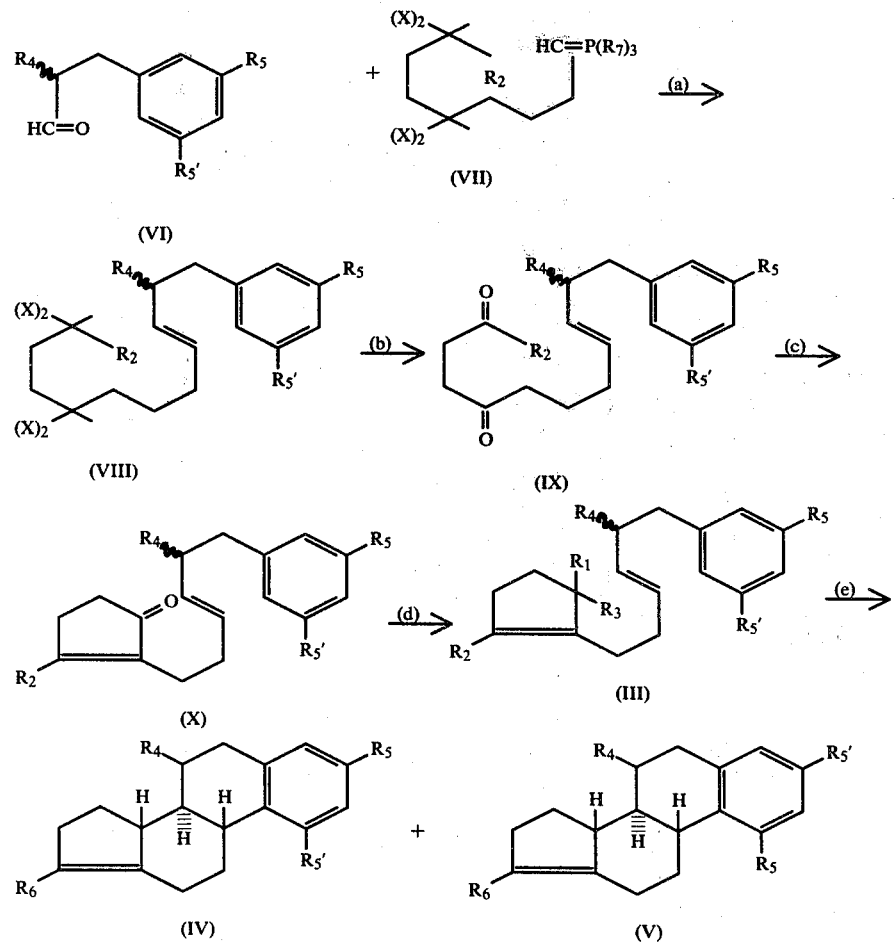

In the Flow Diagram, $R_1$, $R_2$, $R_3$, $R_4$, $R_5$, $R_5'$ and $R_6$ have the meanings previously assigned. $R_7$ is an aryl hydrocarbon group with six or seven carbon atoms, preferably phenyl. X is an alkyl-chalcogen group, that is, alkoxy or alkyl-thio, each of one to about four carbon atoms, and preferably one to about two carbon atoms. The moiety $(X)_2$ is preferably an alkylidene-dichalcogen group, that is: alkylidene-dioxy or alkylidene di-thio with two to about three carbon atoms, for example ethylene-dioxy.

The following may be noted with respect to the substituents $R_1-R_2$ and $R_4-R_6$ inclusive:

One of $R_1$ and $R_2$ is preferably methyl or ethyl, most preferably methyl, while the other substituent is always H. $R_3$ as a "leaving" group is preferably alkoxy of one to four carbon atoms, for example methoxy; otherwise (1) alkoxyalkoxy of two to four carbon atoms, for example methoxymethoxy, 1'-ethoxyethoxy; (2) carboxyacyloxy of one to seven carbon atoms, for example acetoxy, propionyloxy, butyroxy, pivaloyloxy, valeryloxy, benzoyloxy; or (3) trialkylsilyloxy of less than fifteen carbons, for example, trimethylsilyloxy.

$R_4$ is (1) a hydrocarbon group of one to four carbons (preferably alkyl) optionally substituted by halogen, preferably chlorine, or alkoxy of one to two carbon atoms, most preferably methoxy, whereby hydrocarbon is understood to mean a monovalent radical consisting of hydrogen and carbon atoms and which is saturated or unsaturated aliphatic, alicyclic or araliphatic, or (2) more preferably, is alkoxy of one to four carbon atoms, most preferably methoxy.

Examples of $R_4$ hydrocarbons, some optionally substituted, are methyl, ethyl, butyl, chloromethyl, methoxymethyl, allyl, and 2'-chloro-allyl.

$R_5$ and $R_5'$ each are preferably hydroxy, or in the alternative, etherified or esterified hydroxy of less than 10 carbon atoms; for example, (1) hydrocarbyloxy of one to eight carbon atoms, such as methoxy, ethoxy, cyclopentoxy, cyclohexenyloxy, and benzyloxy; (2) α-alkoxyalkoxy of two to four carbon atoms, such as methoxymethoxy, and α-ethoxyethoxy; (3) trimethylsilyloxy, t-butyldimethylsilyloxy, or tetrahydropyranyloxy, carboxyacyloxy of one to seven carbon atoms, such as acetoxy, pivaloyloxy, benzoyloxy.

If $R_5$ and/or $R_5'$ is an oxy group, then the positions 2, 4 and 6 of the phenyl nucleus are activated in the cyclisation. Due to steric factors, position 4 takes no part in the reaction, and for $R_5 \neq R_5'$ two products may therefore be formed as indicated above by the formula IV and V. As previously noted, the ratio of formation of these two products can be changed considerably in favor of one thereof by a suitable choice of $R_5$ and/or $R_5'$. If $R_5$ is, for example, trimethylsilyloxy and $R_5'$ is H, then much more "para" (position 6) product is formed than "ortho" (position 2) product.

If use is made as starting material of a β-arylaldehyde with $R_5$ and/or $R_5'$ being a protected hydroxy group, then the protective group may remain intact during the various reaction steps, but it may also undergo modification. Certain protective groups known to those in the art are preferred for some reaction steps, while again other protective groups are preferred for other reaction steps. In the steps (a) and (b), for example, $R_5$ and/or $R_5'$ is preferably methoxy or methoxymethoxy. In steps (c) and (d), $R_5$ and/or $R_5'$ may without objection be hydroxy, while in step (e) $R_5$ and/or $R_5'$ is preferably trimethylsilyloxy if the interest is primarily for the "position 6" product. Specifically, the "position 6" product for $R_5'$ is H is most preferred since it may be used for the preparation of steroids similar to those occurring in nature.

In order to prepare the diketone of formula IX, it is also possible to start from the β-arylaldehyde of formula VI and allow this to react with 4-(5'-$R_2$-2'-furyl)-butylidene-triarylphosphorane, according to the Wittig-Schlosser reaction, after which the furyl-(E)-olefine thus obtained is hydrolysed with acid, preferably acetic acid in the presence of a catalytic amount of sulphuric acid, and at 100°-110° C.

The cyclisation substrate contains two asymmetric centers, namely, the carbon atom carrying the substituent $R_1$ and the carbon atom carrying the substituent $R_4$. The stereochemistry of the cyclisation product proves to be governed mainly by the latter center. The substituent $R_4$ in the cyclisation product surprisingly proves to occur predominantly in the axial configuration.

If use is made of a racemic cyclisation substrate as starting material, that is, a material with nearly equal amounts of the (R)-$R_4$-substituted and (S)-$R_4$-substituted compounds, then a racemic tetracyclic product consisting of 2 enantiomers is shown to be formed, while on grounds of the two asymmetric centers, without optical induction four stereo-isomers in equal amounts should be formed. That the asymmetric center with the substituent $R_1$ has little, if any, influence on the stereochemistry of the end product is proved by the fact that the (R)-$R_1$-(R)-$R_4$-substituted cyclisation substrate gives the same $R_4$-axially substituted cyclisation product as the (S)-$R_1$-(R)-$R_4$-substituted cyclisation substrate.

It is indicated in formula III that the substituent $R_4$ may be present in the (R)-configuration or the (S)-configuration. If the racemate is used as starting material and the position isomerism of the aromatic ring is neglected, a racemate of an $R_4$-axially substituted steroid compound with formula IV is formed in the cyclisation. If any optically active cyclisation substrate is used as starting material, for example, the (S)-$R_4$-compound ($R_4$ is $CH_3$), then an optically active compound of formula IV ($R_4$ is $CH_3$) is formed.

On rotating formula IV through 180° in the plane of the drawing, it can more readily be established that an ent-7α-$CH_3$ $\Delta^{1,3,5(10),13(17)}$-gonatetraene of formula XI has been formed:

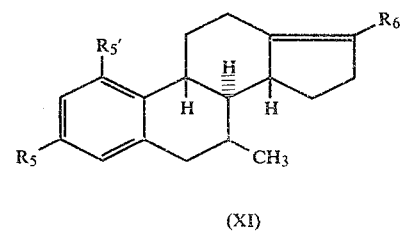

(XI)

By epoxidising this olefine, preferably by conversion into a 13,17-halohydrin, most preferably a chloro- or bromohydrin, and treatment of the halohydrin with a base, the ent-7α-$CH_3$-13α,17α-epoxy compound of formula XII below is formed. (When a per-acid is used for direct epoxidation, the ent-7α-$CH_3$-13β,17β-epoxy compound is formed). Opening of the epoxide ring under weakly acid conditions, preferably by use of an aprotic Lewis acid, for example $BF_3$-di-ethyl ether, is conducive to migration of the substituent $R_6$ from position 17 to position 13, such that the ent-7α-CH₃-13β-R₆-17-ketone of formula XIII is formed from the ent-β-epoxide XII (the ent-α-epoxide gives rise to the ent-7α-CH₃-13α-R₆-17-ketone in this way).

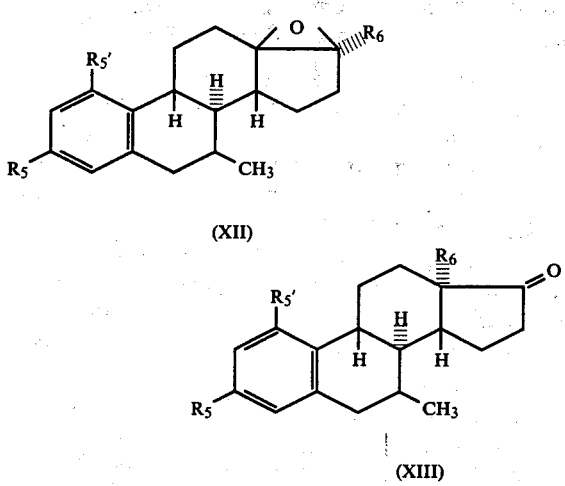

The antipode can be converted into the natural 7α-CH₃-13β-R₆-Δ$^{1,3,5(10)}$-gonatrien-17-one in a corresponding fashion. When R₅ is methoxy, R₅' is hydrogen and R₆ is methyl, the 3-methyl ether of 7α-methyl-oestrone is obtained in this way.

The conversion of the Δ$^{13(17)}$-olefine into the 13,17-halohydrin is carried out with a N-halo-carbonamide or -sulfonamide, such as N-chloro- or N-bromo-succinimide, N-chloro-toluenesulfonamide, in a mixture of water and an organic solvent, such as t-butanol, tetrahydrofuran, dimethoxyethane. Treatment of the 13,17-halohydrin with a base is carried out with an aqueous NaOH- or KOH-solution. The opening of the epoxide ring is carried out in an apolar aprotic solvent, for example hydrocarbons, such as benzene, or halogenated hydrocarbons, such as methylene chloride.

Thus, the present invention provides novel cyclisation substrates which give on cyclisation novel 7α-substituted steroidal cyclisation products. The cyclisation substrates as well as the cyclisation products are important novel intermediates for preparing well-known biological active 7α-substituted steroids.

Although the invention has been described with reference to specific embodiments above, numerous variations and modifications will become evident to those skilled in the art, without departing from the scope and spirit of the invention as described above, defined in the appended claims, and as shown in the following Examples:

EXAMPLE I

Preparation of
dl-3-(m-methoxyphenyl)-2-methyl-1-propanol (Precursor of Compound VI)

A solution of m-bromo-anisole (37.4 g, 0.2 mole) in dry tetrahydrofuran (200 ml) was added dropwise under nitrogen to magnesium shavings (4.8 g, 0.2 at.). The resultant solution was stirred for 30 minutes at room temperature, and was then warmed to 50° C.

Methallyl chloride (20 g, 0.22 mol) was added dropwise over a 30 minute period (weak exothermic reaction) after which the reaction mixture was stirred until it had cooled to room temperature (about 2 hours).

The reaction mixture, containing m-methallylanisole, was then cooled in ice to 5° C., and a solution of diborane in tetrahydrofuran (150 ml, 1 M, 0.15 mol) was added dropwise at such a speed that the temperature remained below but close to 15° C.

The whole was subsequently stirred for 1 hour at room temperature, after which 10% sodium hydroxide (150 ml) was added. While cooling in ice, 40 ml 30% by weight hydrogen peroxide was slowly added dropwise such that the temperature remained at about 40° C. The whole was stirred for a further 1 hour without external cooling. The excess hydrogen peroxide was decomposed by the slow addition of sodium sulphite solution (30 g in 150 ml water) while cooling with ice.

The reaction mixture was mixed with 300 ml N sulphuric acid and extracted with ether (2×250 ml). The extracts were dried with anhydrous sodium sulphate and evaporated to dryness. The residue was chromatographed on 600 g silica gel with hexane/ethyl acetate (80:20), giving 27.3 g (76% yield) of pure product.

EXAMPLE II

Preparation of
dl-3-(m-methoxyphenyl)-2-methylpropanal (formula VI: R₄=CH₃; R₅=OCH₃)

First method. (R₅'=H.)

Pyridinium chlorochromate (32 g, 0.15 mol) was suspended in dry dichloromethane. A single amount of 18 g (0.1 mol) 3-(m-methoxyphenyl)-2-methyl-1-propanol dissolved in dry dichloromethane (50 ml) was then added with vigorous stirring. The mixture was stirred for 2 hours at room temperature and was then mixed with hexane (250 ml) and filtered through HY-FLO ™. The filtrate was distilled under vacuum, giving 13.4 g pure product (75% yield) of boiling point 93°–96° C./0.5 mm.

EXAMPLE III

Preparation of
dl-3-(m-methoxyphenyl)-2-methylpropanol (formula VI: R₄=CH₃; R₅=OCH₃)

Second method. (R₅'=H.)

A mixture of m-bromo-anisole (18.7 g, 0.1 ml), methallyl alcohol (12 g, 0.16 mol), powdered sodium bicarbonate (12 g, 0.14 mol), palladium (II) chloride (0.30 g, 1.7 mmol), triphenylphosphine (0.45 g, 1.7 mmol) and dimethyl formamide was heated with stirring at 130° C. under nitrogen.

The reaction mixture was cooled, mixed with water and extracted with toluene (2×100 ml). The extracts were dried (anhydrous sodium sulphate) and evaporated to dryness, after which the residue was fractionated and distilled under vacuum. This resulted in recovery of 7.7 g starting material, boiling point 56° C./0.2 mm, and 5.9 g of product, boiling point 85°–86° C./0.2 mm yield (yield 33%, or 56% by weight on basis of m-bromo-anisole consumed).

EXAMPLE IV—REACTION (a)

Preparation of
dl-(E)-1-(m-methoxyphenyl)-2-methyl-8,11-bis(ethylenedioxy)-3-dodecene (formula VIII: $R_4=CH_3$; $R_5=OCH_3$; $R_2=CH_3$, $(X)_2$=ethylenedioxy, $R_5'=H$)

Phenyl-lithium in ether (48 ml of a 1.1 M solution, 0.053 mol) was added dropwise under nitrogen to a stirred suspension of 5,8-bis(ethylenedioxy)-nonyl-triphenylphosphonium iodide (Compound VII) (31.6 g, 0.05 mol) in dry tetrahydrofuran, cooled in ice. The red solution was stirred for a further 15 minutes without cooling, after which it was cooled to $-70°$ C. The aldehyde (Examples II and III) (8.72 g, 0.049 mol), dissolved in dry tetrahydrofuran (20 ml), was added dropwise, after which the mixture was stirred for 5 minutes at $-70°$ C. A further quantity of phenyl-lithium in ether (80 ml, 1.1 M, 0.088 mol) was added and the resultant red solution was warmed to $-30°$ C. After 15 minutes, 15 ml methanol was added dropwise. The resultant mixture was mixed with water and extracted with ether. The ether extracts were dried (anhydrous sodium sulphate), filtered and evaporated to dryness under vacuum. The residue was chromatographed on 300 g silica gel with hexane/ethyl acetate 80:20, giving 13.2 g (67% yield) of a colorless oil.

EXAMPLE V—REACTIONS (b) and (c)

Preparation of
dl-3-methyl-2-[(E)-6'-(m-methoxyphenyl)-5'-methyl-3'-hexenyl]-2-cyclopentenone (formula X: $R_4=CH_3$; $R_2=CH_3$; $R_5=OCH_3$; $R_5'=H$)

A solution of the Wittig product from Example IV (10.1 g, 0.025 mol) in 250 ml ethanol (95%) and 125 ml 0.2 N hydrochloric acid was heated at 50°–55° C. for 2 hours to produce the analogue of compound IX, after which 25 ml 2 N NaOH and 225 ml 95% ethanol were added and the resultant solution was refluxed for $2\frac{1}{2}$ hours. The reaction mixture was reduced in volume to about 100 ml by evaporation under vacuum, after which it was extracted with ethyl acetate. The extracts were dried over anhydrous sodium sulphate and evaporated to dryness. The residue was chromatographed on 300 g silica gel with hexane/ethyl acetate 90:10. The product was obtained as a colorless oil (6.3 g, 85% yield).

EXAMPLE VI—REACTION (d)

Preparation of
dl-3-methyl-2-[(E)-6'-(m-methoxyphenyl)-5'-methyl-3'-hexenyl]-2-cyclopentenol (formula III: $R_1=H$; $R_2=CH_3$; $R_3=OH$; $R_4=CH_3$; $R_5=OCH_3$; $R_5'=H$)

Lithium aluminium hydride (0.57 g, 0.015 mol) was slowly added at $-20°$ C. to a solution of the cyclopentenone (Compound X) from Example V (3.0 g, 0.1 mol) in dry ether (100 ml). The mixture was warmed to 0° C. with stirring during a 30 minute period. The excess hydride was decomposed by cautious addition of saturated sodium sulphate solution. The ether layer was decanted from the resultant suspension. The suspension was washed twice with dry ether and the combined ethereal solutions were evaporated to dryness, giving 3.0 g (99% yield) product in the form of a colorless oil, which was not subjected to further purification.

EXAMPLE VII—REACTION (e)

Preparation of dl-1- and -3-methoxy-7α,17-dimethyl $\Delta^{1,3,5(10),13(17)}$-gonatetraene (formulae IV and V: $R_4=CH_3$; $R_5=OCH_3$; $R_6=CH_3$, $R_5'=H$)

2.7 ml stannic chloride (7.3 g, 0.028 mol) was added dropwise at $-70°$ C. under a nitrogen atmosphere to a solution of the cyclopentenol (Example VI) (3.0 g, 0.01 mol) in 165 ml dichloromethane. The mixture thus obtained was stirred for 15 minutes at $-70°$ C., after which a solution of NaOH (3.3 g) in methanol (40 ml) was added dropwise such that the temperature did not rise above $-60°$ C. The mixture obtained was diluted with ether and shaken with 85 ml 10% sodium hydroxide. The organic layer was separated and dried over anhydrous potassium carbonate. The solvents were removed by evaporation, and the residue (2.9 g) was chromatographed on 60 g silica gel with hexane/toluene 80:20 (400 ml) and hexane/toluene 70:30 (300 ml). Initially 0.90 g of a solid substance was obtained (melting point 100°–120° C.), and after crystallization from ethanol 0.79 g, melting point 120°–122° C. (28% by weight yield), consisting of the 1-methoxy-7α-methyl isomer. 1.10 g oil was subsequently isolated and on crystallization from ethanol this gave 0.80 g crystals, melting point 55°–60° C. (28% yield, consisting of the 3-methoxy-7α-methyl isomer). Evaporation of the mother liquors to dryness gave 0.30 g oil which consisted mainly of a mixture of the 3-methoxy-7α and 7β-methyl isomers.

EXAMPLE VIII

Preparation of dl-7α-methyloestrone, 3-methyl ether (formula XIII: $R_5=OCH_3$; $R_6=CH_3$, $R_5'=H$)

A solution of 3-methoxy-7α-methyl-17-methyl-$\Delta^{1,3,5}$-gonatetraene (0.282 g, 0.001 mol) in t.butanol/water 9:1 (30 ml) was cooled in ice. N-chlorosuccinimide (0.265 g, 0.002 mol) was added to the suspension thus obtained, after which the reaction mixture was stirred for 1 hour at room temperature. Sodium bisulphite (0.10 g) and 10 ml 20% KOH solution were then added consecutively and the whole was stirred for 30 minutes at room temperature. Hexane (50 ml) was then added and the resultant aqueous layer was removed. The organic layer was evaporated to dryness under vacuum.

The residue, consisting of the 13α17α-epoxy derivative (Compound XII), was taken up in toluene (30 ml) and treated with boron trifluoride etherate (2 ml) for 1 minute at room temperature. The dark red reaction mixture was diluted with ether and shaken with saturated sodium bicarbonate solution. The organic layer was separated, dried over anhydrous $Na_2SO_4$, and evaporated to dryness. The residue was chromatographed on 30 g silica gel with hexane/ethyl acetate 9:1.

The product obtained was crystallized from ether/pentane, giving 107 mg of product, melting point 138°–142° C. (36% yield).

EXAMPLE IX

Preparation of
dl-(E)-1-(m-hydroxyphenyl)-2-methyl-8,11-bis-(ethylenedioxy)-3-dodecene (formula VIII: $R_2=CH_3$; $R_5=OH$; $(X)_2=$ethylenedioxy, $R_5'=H$)

A solution of (E)-1-(m-methoxyphenyl)-2-methyl-8,11-bis(ethylenedioxy)-3-dodecene (1.21 g, 0.003 mol, in Example IV) and KOH (1.6 g) in tri-ethylene glycol (16 ml) was heated at 200° C. for 2 hours. The reaction mixture was cooled, diluted with water, acidified with 4 N hydrochloric acid and extracted with chloroform (3×20 ml). The extracts were dried (anhydrous $Na_2SO_4$) and evaporated to dryness. The residue was chromatographed on 35 g silica gel with hexane/ethyl acetate, 80:20 followed by 60:40.

In this way, 0.55 g of the starting material was obtained, followed by 0.41 g product as a colorless oil. Yield 64% on the basis of starting material consumed.

EXAMPLE X—STEP (c)

Preparation of
dl-3-methyl-2-[(E)-6'-(m-hydroxyphenyl)-5'-methyl-3'-hexenyl]-2-cyclopentenone (formula X: $R_2=CH_3$; $R_4=CH_3$; $R_5=OH$), $R_5'=H$.)

The product from Example IX (0.41 g) was caused to react in a way similar to that given in Example V. The reaction product was obtained as a colorless oil, 0.25 g, 84% by weight yield.

EXAMPLE XI

Preparation of
dl-3-methyl-[(E)-6'-(m-t-butyl-dimethylsilyloxy-phenyl)-5'-methyl-3'-hexenyl]-2-cyclopentenone (formula X: $R_2=CH_3$; $R_4=CH_3$; $R_5=$t-butyl-dimethylsilyloxy, $R_5'=H$).

The product from Example X (0.25 g, 0.9 mmol) was dissolved in dry dimethylformamide (1 ml). Imidazole (0.48 g, 7 mmol) and t-butyldimethylchlorosilane (0.30 g, 2 mmol) were added. After stirring for 3 hours at 38° C., water was added and the mixture obtained was extracted with ether. The extract was dried (anhydrous $Na_2SO_4$) and evaporated to dryness. The residue was purified by chromatography (silica gel, hexane/ethyl acetate 80:20), giving 0.30 g product (85% yield) in the form of an oil.

EXAMPLE XII—STEPS (d) AND (e)

Preparation of dl-1- and 3-t-butyldimethylsilyloxy-7α,17-dimethyl-$\Delta^{1,3,5(10),13(17)}$-gonatetraene (formulae IV and V: $R_4=CH_3$; $R_5=$t-butyldimethylsilyloxy; $R_6=CH_3$; $R_5'=H$)

The product of Example XI (0.03 g) was reduced in a way analogous to that described in Example VI (Compound III). The cyclopentenol obtained was subsequently cyclised in a way corresponding to that of Example VII. The product mixture obtained from this reaction was separated by chromatography on silica gel, with hexane followed by hexane/toluene 9:1. In this way, the 1-silyloxy compound was first isolated (40 mg), followed by the 3-silyloxy compound (140 mg), both in the form of oils.

EXAMPLE XIII—REACTION (f)

Preparation of
dl-1-(m-methoxyphenyl)-2-hydroxy-8,11-bis-(ethylenedioxy)-3-dodecyne (formula XVI: $R_2=CH_3$; $R_5=OCH_3$; $R_5'=H$; $(X)_2=$ethylenedioxy.)

A 2 M solution of butyl-lithium in hexane (1.5 ml, 3 mmol) was added dropwise under nitrogen to a solution of 6.9-bis(ethylenedioxy)-1-decyne (0.76 g, 3 mmol) in dry tetrahydrofuran (15 ml). After stirring for 10 minutes, a solution of m-methoxyphenylacetaldehyde (0.45 g, 3 mmol) in dry THF (10 ml) was added dropwise. The mixture was stirred for 1 hour, mixed with water, and extracted with ethylacetate. The extracts were dried over anhydrous $Na_2SO_4$ and evaporated to dryness. The residue was purified by chromatography with ether on 30 g silica gel, giving 0.76 g (63% yield) of product in the form of a colorless oil.

EXAMPLE XIV—REACTION (g)

Preparation of
dl-(E)-1-(m-methoxyphenyl)-2-hydroxy-8,11-bis(ethylenedioxy)-3-dodecane (formula VIII: $R_2=CH_3$; $R_4=OH$; $R_5=OCH_3$; $(X)_2=$ethylenedioxy, $R_5'=H$)

A solution of the product from Example XIII (0.76 g) and lithium aluminium hydride (0.40 g) in dry tetrahydrofuran (20 ml) was heated for 4 hours at 58° C. The reaction mixture was cooled and the excess hydride was decomposed by addition of damp ether. The solution obtained after filtration was evaporated to dryness and the residue was chromatographed on 20 g silica gel with hexane/ethyl acetate 60:40, giving 0.50 g product (65% yield) in the form of a colorless oil.

EXAMPLE XV—REACTION (h)

Preparation of
dl-(E)-1-(m-methoxyphenyl)-2-methoxy-8,11-bis(ethylenedioxy)-3-dodecene (compound VIII: $R_2=CH_3$; $R_4=OCH_3$; $R_5=OCH_3$; $(X)_2=$ethylenedioxy, $R_5'=H$)

The product from Example XIV (0.50 g) was dissolved in a mixture of dry tetrahydrofuran (14 ml) and hexamethylphosphoramide (1.4 ml). Sodium hydride (0.20 g, 50% suspension in mineral oil) and methyl iodide (2 ml) were added, and the resultant mixture was stirred for 2 hours at room temperature.

The reaction mixture was mixed with ether (50 ml) and washed with water. Drying, and removal of solvent by evaporation, gave a residue which was purified by chromatography on silica gel (20 g) with hexane/ethyl acetate 80:20, followed by 60:40.

The pure product was obtained as an oil, 0.40 g (77% yield).

EXAMPLE XVI (REACTIONS (b) AND (c))

Preparation of
dl-3-methyl-2-[(E)-6'-(m-methoxyphenyl)-5'-methoxy-3'-hexenyl]-2-cyclopentenone (compound X: $R_2=CH_3$; $R_4=OCH_3$; $R_5=OCH_3$, $R_5'=H$)

In a way analogous to that of Example V, the product of Example XV was converted to the corresponding cyclopentenone, which was obtained as a colorless oil in a yield of 77% (0.23 g).

EXAMPLE XVII—REACTION (d)

Preparation of dl-1,7α- and dl-3,7α-dimethoxy-17-methyl-$\Delta^{1,3,5(10),13(17)}$-gonatetraene (compounds IV, V: $R_5=OCH_3$; $R_4=OCH_3$; $R_6=CH_3$, $R_5'=H$)

The product from Example XVI (0.15 g) was reduced in a way analogous to that described in Example VI. The product thus obtained (0.145 g) was dissolved in 3 ml dry dichloromethane and added to a solution of stannic chloride (0.15 ml) previously cooled to $-70°$ C., in dry dichloromethane (10 ml). After stirring for 30 minutes at $-70°$ C., a solution of NaOH (1.0 g) in 90% methanol (10 ml) was added dropwise. The mixture was diluted with ether, washed with water, dried (anhydrous $Na_2SO_4$) and evaporated to dryness. The residue was chromatographed on 25 g silica gel with toluene. The 1,7α-dimethoxy compound (30 mg, melting point 131°–134° C.) and the 3,7α-dimethoxy compound (40 g, melting point 110°–114° C.) were eluted consecutively. Further elution yielded a small amount of the 3,7β-dimethoxy compound.

EXAMPLE XVIII

Preparation of 2-(4-bromobutyl)furan

A solution of furan (23.8 g, 0.35 mol) in dry tetrahydrofuran (150 ml) was cooled to $-15°$ C. A solution of n-butyl-lithium in hexane (150 ml, 2.2 M, 0.33 mol) was then added dropwise under nitrogen and the reaction mixture was then stirred for a further 2½ hours at 0° C. The solution thus obtained was subsequently added over a period of about 1 hour under nitrogen to a solution of 1,4-dibromobutane (150 g, 0.7 mol) in dry tetrahydrofuran (225 ml) at $-25°$ C.

The mixture obtained was stirred for a further 3 hours at 0° C. and for 15 hours at room temperature. A saturated cooking salt solution (200 ml) was then added, and the organic layer was removed and dried (anhydrous $MgSO_4$). Distillation under vacuum with the aid of a VIGREUX TM apparatus gave 44 g pure product (66% yield).

EXAMPLE XIX

Preparation of 8-bromo-1,4-bis(ethylenedioxy)octane

A mixture of the 2-(4-bromobutyl)furan of Example XX (20.3 g, 0.1 mol), benzene (120 ml), glycol (120 ml), concentrated sulphuric acid (12 ml) and tetra-n-butylammonium bromide (1.2 g) was boiled for 96 hours with the aid of an azeotropic water separator. The reaction mixture was cooled, and the benzene layer was separated. The glycol layer was washed with a few portions of benzene, after which the combined benzene layers were washed with saturated sodium bicarbonate until neutral. The benzene solution was dried over anhydrous $MgSO_4$ and solvent was removed by evaporation. The residue was chromatographed on silica gel (200 g) with hexane/ethyl acetate 8:2. This resulted in 7.5 g product (24% by weight yield) in the form of a colorless oil.

EXAMPLE XX

Preparation of 8-iodo-1,4-bis(ethylenedioxy)octane

The bromide from Example XIX (7.5 g, 0.024 mol) was dissolved in butan-2-one (70 ml), after which powdered potassium iodide (6.8 g, 0.04 mol) and pyridine (0.2 ml) were added. The mixture was refluxed for 1½ hours, mixed with ether, and filtered. Evaporation yielded 8.2 g product (95% by weight yield).

EXAMPLE XXI

Preparation of 5,8-bis(ethylenedioxy)octyl-triphenyl phosphonium iodide

The iodide from Example XX (8.2 g, 0.023 mol) and triphenylphosphine (10 g, 0.038 mol) were dissolved in benzene (70 ml). The solution was boiled with stirring for 16 hours. After cooling, the benzene layer was decanted and the viscous residue was dissolved in a little acetone. Addition of ether gave 5.01 g (35% by weight yield) of a crystalline product, melting point 102°–104° C., while dilution of the mother liquor with ether gave a further 6.0 g (42% by weight yield) of less pure product (oil).

EXAMPLE XXII—STEP (a)

Preparation of dl-(E)-1-(m-methoxyphenyl)-2-methyl-8,11-bis(ethylenedioxy)-3-undecene (formula VIII, $R_2=H$; $R_4=CH_3$; $R_5=OCH_3$; $(X)_2=$ethylenedioxy, $R_5'=H$)

5,8-bis(ethylenedioxy)octyl-triphenylphosphonium iodide (3.1 g, 0.005 mol) was caused to react with dl-3-(m-methoxyphenyl)-2-methylpropanol (0.89 g, 0.005 mol) in a way fully analogous to that described in Example IV, giving 1.22 g pure product (63% yield).

EXAMPLE XXII—STEPS (b) AND (c)

Preparation of dl-2-[(E)-6'-(m-methoxyphenyl)-5'-methyl-3'-hexenyl]-2-cyclopentenone (formula X: $R_2=H$; $R_4=CH_3$; $R_5=OCH_3$, $R_5'=H$)

The product from Example XXII (1.22 g, 3.1 mol) was dissolved in a mixture of dimethoxyethane (120 ml) and N hydrochloric acid (40 ml). The solution was heated under nitrogen for 2½ hours at 50°–60° C., cooled, and concentrated under vacuum to about 50 ml. The residue was extracted with ether (3×). The ether extracts were dried (anhydrous $Na_2SO_4$) and evaporated to dryness. The residue (0.95 g), dissolved in a mixture of 190 ml 95% ethanol and 25 ml 0.2 N potassium hydroxide, was heated at 50° C. under nitrogen for 6 hours. The product was isolated in a way analogous to that described in Example VI, giving 0.35 g of a pure product (39% yield) in the form of a somewhat unstable colorless oil.

EXAMPLE XXIV—STEP (d)

Preparation of dl-2-[(E)-6'-(m-methoxyphenyl)-5'-methyl-3'-hexenyl]-1-methyl-2-cyclopenten-1-ol (formula III: $R_2 \times H$; $R_1=CH_3$; $R_3=OH$; $R_4=CH_3$; $R_5=OCH_3$, $R_5'=H$)

The product from Example XXIII (0.284 g, 1 mmol) was dissolved in dry ether (15 ml) and cooled to $-70°$ C. under nitrogen. Excess methyl-lithium in ether (1.5 ml, 2 M, 3 mmol) was added. After stirring for a further 10 minutes at −70° C., a few drops of saturated sodium sulphate solution were added. The mixture obtained was warmed, filtered and evaporated to dryness, giving the product in quantitative yield (0.30 g) in the form of a colorless oil.

EXAMPLE XXV—STEP (e)

Preparation of dl-1-methoxy- and dl-3-methoxy-7α,17dimethyl-Δ$^{1,3,5(10),13(17)}$gonatetraene (formulae IV and V: $R_6=CH_3$; $R_4=CH_3$; $R_5=OCH_3$, $R_5'=H$)

The product from Example XXIV (0.30 g) was cyclised in the way described in Example VII to give the 1-methoxy 7α-methyl-compound (0.07 g, melting point 119°–122° C.) and the 3-methoxy-7α-methyl-compound (0.08 g, melting point 55°–60° C.).

EXAMPLE XXVI

Preparation of dl-3-(m-methoxyphenyl)-2-methoxymethyl-propan-1-ol

Methyl-3-(m-methoxyphenyl)propionate (9.7 g, 0.05 mol) was added dropwise to a solution of lithium di-isopropylamide (0.05 ml) cooled to −78° C.; this latter solution had been obtained by mixing 5 g di-isopropylamine in dry tetrahydrofuran (50 ml) with butyl-lithium in hexane (23 ml, 2.16 M) at 0° C. under nitrogen. After stirring for 10 minutes at −78° C., chlorodimethyl ether (4.8 g, 0.06 mol) dissolved in dry hexamethyl-phosphoric acid triamide (4.5 g) was slowly added dropwise.

After stirring for a further 10 minutes, the reaction mixture was warmed to 0° C., mixed with water, and extracted with ether. The ether extracts were dried (anhydrous $Na_2SO_4$) and evaporated to dryness. The residue was chromatographed on silica gel with hexane/ethyl acetate 80:20, giving 9.5 g methyl dl-3-(m-methoxyphenyl)-2-methoxymethyl-propionate in the form of a colorless oil (80% yield).

A solution of this ester (4.7 g, 0.02 mol) in dry ether (20 ml) was added to a suspension of lithium aluminium hydride (0.75 g, 0.02 mol) in dry ether (20 ml) cooled in ice. The reaction mixture was stirred for 1 hour at room temperature, after which saturated sodium sulphate solution was added dropwise with cooling. After filtering and removing solent by evaporation, 4.1 g product was obtained (100% yield) in the form of a colorless oil.

EXAMPLE XXVII INTER ALIA, REACTIONS (a)-(d)

Preparation of dl-3-(m-methoxyphenyl)-2-methoxymethylpropanal (formula VI: $R_4=CH_2OCH_3$; $R_5=OCH_3$; $R_5'=H$) and dl-7α-methoxymethyloestrone The product of Example XXVI was oxidised in a way analogous to that described in Example II. The crude product was purified by chromatography on silica gel with hexane/ethyl acetate 80:20, giving a pure product, in the form of a colorless oil, in a yield of 74%.

The aldehyde obtained was converted, in an similar fashion to that described in the Examples IV-VI, into dl-3-methyl-2-[(E)-6'-(m-methoxyphenyl)-5'-methoxymethyl-3'-hexenyl]-2-cyclopentenol, which was cyclised and converted into the 3-methyl ether of dl-7α-methoxymethyloestrone in a way similar to that described in Examples VII and VIII.

EXAMPLE XXVIII—RECATIONS (a)-(e)

Preparation of dl-7α,18-dimethyloestrone, 3-methyl ether

In a way similar to that described in the Examples IV-VIII, the 3-methyl ether of dl-7α,18-dimethyloestrone was obtained starting from dl-3-(m-methoxyphenyl)-2-methylpropanal and 5,8-bis(ethylenedioxy)-decycltriphenyl phosphonium iodide. (Physical constants gonatetraenes: see Example XXXVI).

EXAMPLE XXIX

Preparation of dl-3-(3,5-dimethoxyphenyl)-2-methylpropionic acid ethylester

Ethylpropionate (10.2 g; 0.1 mol) was added dropwise to a solution of lithium-di-isopropylamide (0.1 mol) which was obtained by mixing at 0° C. under nitrogen 10 g di-isopropylamine in 100 ml dry tetrahydrofuran with n-butyllithium in hexane (45.5 ml; 2.2 M). After the addition of ethylpropionate (which was carried out at a temperature of −78° C.) the mixture was stirred at −78° C. for 10 minutes, whereafter a solution of 1,3-dimethoxybenzylbromide (23.0 g; 0.1 mol) in dry hexamethylphosphoric acid triamide (9 g) was added dropwise. The mixture was stirred at −70° C. for 10 minutes and then heated to 0° C. Water was added and the mixture was extracted with ether. The ether-extract was dried on $Na_2SO_4$ and the solvent was evaporated. Destillation of the residue in vacuum gave 19.4 g pure product (77% yield), boiling point 150°–155° C./0.2 mm.

EXAMPLE XXX

Preparation of dl-3-(3,5-dimethoxyphenyl)-2-methylpropanal (formula VI: $R_4=CH_3$; $R_5=OCH_3$; $R_5'=OCH_3$)

The ester of Example XXIX (12.6 g; 0.05 mol) was dissolved in dry toluene (100 ml). The solution was cooled under nitrogen to −70° C. and a solution of di-isobutylaluminiumhydride in toluene (44 ml; 1.2 M; 0.053 mol) was added dropwise in 15 minutes. The mixture obtained was stirred at −70° C. for 30 minutes, then mixed with water and ether and heated to room temperature. Sulphuric acid (2 N) was added until a clear solution was obtained. The organic layer was separated, washed with a sodium-bicarbonate-solution and dried on $Na_2SO_4$. Evaporation of the solvent gave 10.2 g (98% yield) product.

EXAMPLE XXXI—REACTION (a)

Preparation of dl-(E)-1-(3,5-dimethoxyphenyl)-2-methyl-8,11-bis-(ethylenedioxy)-3-dodecene (formula VIII: $R_2=CH_3$; $R_4=CH_3$; $R_5=OCH_3$; $R_5'=OCH_3$; $(X)_2=$ethylenedioxy)

5,8-bis(ethylenedioxy)-nonyltriphenylphosphoniumiodide (10.2 g; 0.049 mol) was caused to react with dl-3-(3,5-dimethoxyphenyl)-2-methylpropanal (10.2 g, 0.049 mol) in a way fully analogous to that described in Example IV, giving 17.0 g (80% yield) product in the form of a colourless oil.

EXAMPLE XXXII—REACTIONS (b) AND (c)

Preparation of
dl-3-methyl-2-[(E)-6'-(3,5-dimethoxyphenyl)-5'-methyl-3'-hexenyl]-2-cyclopentenone (formula X: $R_2=CH_3$; $R_4=CH_3$; $R_5=OCH_3$; $R_5'=OCH_3$)

The product of Example XXXI (17.0 g; 0.039 mol) was converted in a way analogous to that described in Example V into the desired product (10.9 g; 85% yield, colourless oil).

EXAMPLE XXXIII—REACTIONS (d) AND (e)

Preparation of
dl-1,3-dimethoxy-7α,17-dimethyl-$\Delta^{1,3,5(10),13(17)}$-gonatetraene (formula IV, V: $R_4=CH_3$; $R_5=OCH_3$; $R_5'=OCH_3$; $R_6=CH_3$)

The product of Example XXXII (3.3 g; 0.01 mol) was reduced in a way analogous to that described in Example VI and the reaction product was cyclised in a way analogous to that described in Example VII. The cyclisation product was purified by chromatography on silicagel with hexane/ethylacetate 9:1, yielding 2.2 g product (70% yield, m.p. 80°–90° C.).

EXAMPLE XXXIV

Preparation of
dl-1,3-dimethoxy-7α-methyl-$\Delta^{1,3,5(10)}$-oestratriene-17-one (formula XIII: $R_5=OCH_3$; $R_5'=OCH_3$; $R_6=CH_3$)

The product of Example XXXIII (1.56 g; 5 mmol) was converted into the corresponding oestrone derivative in a way analogous to that described in Example VIII. Yield 0.36 g (23%) product in the form of colourless crystals, m.p. 135°–140° C.

EXAMPLE XXXV

Preparation of
dl-2-[(E)-6'-(m-methoxyphenyl)-5'-methyl-3'-hexenyl]-1-ethyl-2-cyclopenten-1-ol (formula III: $R_2=H$; $R_1=C_2H_5$; $R_3=OH$; $R_4=CH_3$; $R_5=OCH_3$; $R_5'=H$)

In a similar way as described in Example XXIV the product of Example XXIII (0.284 g, 1 mmol) was converted with excess ethyl-lithium into the desired product (0.3 g), $R_f$ (hexane/ethylacetate 8:2): 0.30 (SiO$_2$); NMR(CDCl$_3$): δ 0.93 (d, J=6, C-5'-methyl), 0.79 and 1.23 (t, J=7 and q, J=7, C$_2$H$_5$), 3.74 (s, OCH$_3$), 5.3 (m, olefinic protons).

EXAMPLE XXXVI

Preparation of dl-1-methoxy- and dl-3-methoxy-7α-methyl-17-ethyl-$\Delta^{1,3,5(10),13(17)}$-gonatetraene (formulae IV and V: $R_6=C_2H_5$; $R_4=CH_3$; $R_5=OCH_3$; $R_5'=H$)

In a similar way as described in Example VII the product of Example XXXV (0.3 g) was cyclised to give 0.05 g 1-methoxy compound (m.p. 95°–100° C.; R$_f$(hexane/toluene 7:3)=0.58) and 0.07 g 3-methoxy compound (oil; R$_f$ (hexane/toluene 7:3)=0.35; NMR (CDCl$_3$): δ 0.86 (d, J=7, 7α-CH$_3$), 0.95 and 2.05 (t, J=7 and q, J=7, 17-C$_2$H$_5$), 3.75 (s, OCH$_3$).

Physical constants of oily cyclisation substrates (cyclopentenols) and oily cyclisation products (7α-substituted $\Delta^{1,3,5(10),13(17)}$-gonatetraenes) according to the invention:

The cyclopentenol of Example VI: R$_f$(hexane/ethylacetate 6:4): 0.47 (SiO$_2$); NMR (CCl$_4$): δ 0.93 (d, J=6, C-5'-methyl), 1.59 (s, C-3-methyl), 3.70 (s, OCH$_3$), 4.5 (m, H at C-1), 5.26 (m, olefinic protons).

dl-3-Methyl-[(E)-6'-(m-t-butyl-dimethylsilyloxy-phenyl)5'-methyl-3'-hexenyl]-2-cyclopentenol (intra Example XII): R$_f$(hexane/ethylacetate 8:2): 0.27 (SiO$_2$); NMR (CCl$_4$): δ 0.17 (s, Si(CH$_3$)$_2$), 0.95 (d, J=6, C-5'-methyl), 0.97 (s, Si-t-C$_4$H$_9$), 1.60 (s, C-3-methyl), 4.5 (m, H at C-1), 5.3 (m, olefinic protons).

The 1-silyloxy-gonatetraene of Example XII: R$_f$(hexane/toluene 9:1): 0.47 (SiO$_2$); NMR (CDCl$_3$): δ 0.15 (s, Si-CH$_3$), 0.23 (s, Si-CH$_3$), 0.75 (d, J=6.5, 7α-CH$_3$), 1.0 (s, Si-t-C$_4$H$_9$), 1.63 (s, 17-CH$_3$).

The 3-silyloxy-gonatetraene of Example XII: R$_f$(hexane/toluene 9:1): 0.36 (SiO$_2$); NMR (CDCl$_3$): δ 0.17 (s, Si(CH$_3$)$_2$), 0.83 (d, J=7, 7α-CH$_3$), 0.97 (s, Si-t-C$_4$H$_9$), 1.61 (s, 17-CH$_3$).

dl-3-Methyl-2-[(E)-6'-(m-methoxyphenyl)-5'-methoxy-3'-hexenyl]-2-cyclopentenol (intra Example XVII): R$_f$(hexane/ethylacetate 6:4): 0.27 (SiO$_2$); NMR (CDCl$_3$): δ 1.60 (s, C-3-methyl), 3.21 (s, C-5'-OCH$_3$), 3.79 (s, Ar-OCH$_3$), 3.70 (q, J=7, C-5'-H), 4.55 (m, C-1-H), 5.4 (m, olefinic protons).

The cyclopentenol of Example XXIV: R$_f$ (hexane/ethylacetate 8:2): 0.31 (SiO$_2$); NMR (CCl$_4$): δ 0.93 (d, J=6, C-5'-methyl), 1.25 (s, C-1-methyl), 3.70 (s, OCH$_3$), 5.1–5.5 (m, olefinic protons).

The cyclopentenol of Example XXVII: R$_f$ (hexane/ethylacetate 6:4): 0.31 (SiO$_2$); NMR (CDCl$_3$): δ 1.60 (s, C-3-methyl), 3.24 (d, J=6, C-5'-CH$_2$-O), 3.28 (s, OCH$_3$), 3.74 (s, OCH$_3$), 4.55 (m, C-1-H), 5.30 (m, olefinic protons).

3-Methoxy-7α-methoxymethyl-$\Delta^{1,3,5(10),13(17)}$-gonatetraene (intra Example XXVII): R$_f$(toluene): 0.17 (SiO$_2$) NMR (CDCl$_3$): δ 1.62 (s, 17-CH$_3$), 3.25 (s, OCH$_3$), 3.75 (s, OCH$_3$), 3.12 and 3.50 (d, J=10 and dd J=4 and 10, 7α-CH$_2$OR). (The 1-methoxy isomer, obtained as a byproduct, is a crystalline substance melting at 155°–158° C.).

dl-3-ethyl-2-[(E)-6'-(m-methoxyphenyl)-5'-methyl-3'-hexenyl]-2-cyclopentenol (intra Example XXVIII): R$_f$ (hexane/ethylacetate 6:4): 0.49 (SiO$_2$); NMR (CDCl$_3$): δ 0.95 (d, J=6, C-5'-methyl), 0.91 and 1.97 (t, J=7 and q, J=7, C$_2$H$_5$), 3.75 (s, OCH$_3$), 4.5 (m, H at C-1), 5.3 (m, olefinic protons).

dl-3-Methyl-2-[(E)-6'-(3,5-dimethoxyphenyl)-5'-methyl-3'-hexenyl]-2-cyclopentenol (intra Example XXXIII): R$_f$ (hexane/ethylacetate 6:4): 0.40 (SiO$_2$); NMR (CDCl$_3$): δ 0.94 (d, J=6, C-5'-CH$_3$), 1.60 (s, C-3-methyl), 3.76 (s, 2x OCH$_3$), 4.5 (m, H at C-1), 5.3 (m, olefinic protons).

What is claimed is:

1. A compound of the formula

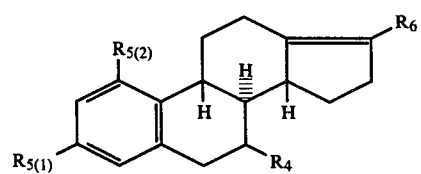

wherein:

(a) $R_4$ is a hydrocarbyl of one to two carbons substituted by halogen or alkoxy of one to two carbons, or alkoxy of one to four carbons;

(b) $R_{5(1)}$ and $R_{5(2)}$ are each H, alkyl, hydroxy, esterified hydroxy group of one to about ten carbons or etherified hydroxy group of one to about ten carbon atoms; and (c) $R_6$ is an alkyl of one to about four carbon atoms.

2. A compound as recited in claim 1 wherein $R_{5(1)}$ is $OCH_3$, $R_{5(2)}$ is H, $R_4$ is selected from the group consisting of $OCH_3$ and $CH_2OCH_3$, and $R_6$ is $CH_3$.

3. A compound as recited in claim 1 wherein $R_{5(1)}$ is H, $R_{5(2)}$ is $OCH_3$, $R_4$ is selected from the group consisting of $OCH_3$ and $CH_2OCH_3$ and $R_6$ is $CH_3$.

4. A compound of the formula:

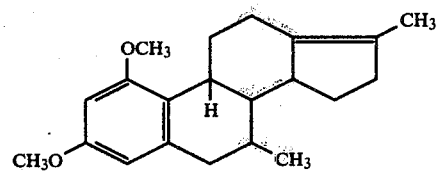

* * * * *

UNITED STATES PATENT OFFICE
CERTIFICATE OF CORRECTION

Patent No. 4,177,197  Dated December 4, 1979

Inventor(s) Filippus J. Zeelen and Marinus B. Groen

It is certified that error appears in the above-identified patent and that said Letters Patent are hereby corrected as shown below:

In the Abstract, correct the figure for formula IV, "para", to

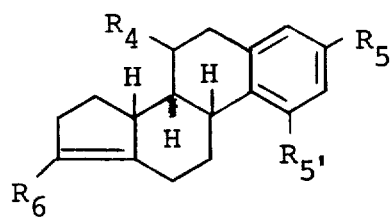

In column 5, in the flow chart, correct formula VIII to:

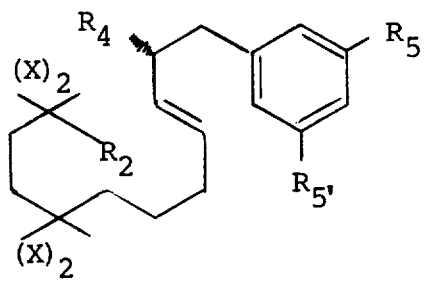

In column 12, line 43, replace "$\Delta^{1,3,5}$—" by --$\Delta^{1,3,5(10)13(17)}$--

In column 13, line 38, delete "$CH_3$" (subscripted) for $R_4$ and replace it by --$CH_3$--.

UNITED STATES PATENT OFFICE

CERTIFICATE OF CORRECTION

Patent No. 4,177,197           Dated   December 4, 1979

Inventor(s) Filippus J. Zeelen and Marinus B. Groen

It is certified that error appears in the above-identified patent and that said Letters Patent are hereby corrected as shown below:

In column 16, line 65, delete "X" between "$R_2$" and "H", and replace by -- = --.

In column 18, line 34, <u>underline</u> "in vacuum".

Signed and Sealed this

Eighth Day of April 1980

[SEAL]

Attest:

SIDNEY A. DIAMOND

Attesting Officer     Commissioner of Patents and Trademarks